United States Patent
Shuppo

(10) Patent No.: US 9,504,510 B2
(45) Date of Patent: Nov. 29, 2016

(54) CRYOGENIC DEVICE

(71) Applicant: Vladimir Shuppo, Montreux (CH)

(72) Inventor: Vladimir Shuppo, Montreux (CH)

( * ) Notice: Subject to any disclaimer, the term of this patent is extended or adjusted under 35 U.S.C. 154(b) by 157 days.

(21) Appl. No.: 14/395,665

(22) PCT Filed: May 29, 2013

(86) PCT No.: PCT/EP2013/061068
§ 371 (c)(1),
(2) Date: Oct. 20, 2014

(87) PCT Pub. No.: WO2014/090418
PCT Pub. Date: Jun. 19, 2014

(65) Prior Publication Data
US 2015/0094702 A1  Apr. 2, 2015

(30) Foreign Application Priority Data
Dec. 11, 2012 (CH) ........................... 2772/12

(51) Int. Cl.
*A61B 18/02* (2006.01)
*A61F 7/00* (2006.01)
*A61H 33/06* (2006.01)
*F25D 3/10* (2006.01)

(52) U.S. Cl.
CPC .............. *A61B 18/02* (2013.01); *A61F 7/0053* (2013.01); *A61H 33/066* (2013.01); *A61H 2033/062* (2013.01); *A61H 2201/5007* (2013.01); *A61H 2201/5035* (2013.01); *A61H 2201/5038* (2013.01); *A61H 2201/5043* (2013.01); *A61H 2201/5082* (2013.01); *A61H 2201/5097* (2013.01); *A61M 2205/3606* (2013.01); *F25D 3/102* (2013.01)

(58) Field of Classification Search
CPC ..................... A61F 7/0053; A61F 2007/0056; A61F 2007/0057; A61F 2007/0061; A61B 18/02
See application file for complete search history.

(56) References Cited

U.S. PATENT DOCUMENTS

| | | | | |
|---|---|---|---|---|
| 2,817,340 A | * | 12/1957 | Cuvier | A61F 7/0053 607/80 |
| 3,902,488 A | * | 9/1975 | Sheppard | A61F 7/0053 128/200.14 |
| 4,784,140 A | * | 11/1988 | Donnerback | A61F 7/0053 128/DIG. 27 |
| 4,838,270 A | | 6/1989 | Donnerhack et al. | |
| 5,817,147 A | * | 10/1998 | Wolf | A61F 7/00 126/204 |

(Continued)

OTHER PUBLICATIONS

International Search Report for corresponding International Application No. PCT/EP2013/061068, mailed Aug. 2, 2013 (3 pages).

*Primary Examiner* — Jocelyn D Ram
(74) *Attorney, Agent, or Firm* — Osha • Liang LLP

(57) ABSTRACT

Cryogenic device for carrying out cryotherapy on the entire body of a patient, the cryogenic device includes a treatment cabin for taking up a patient, the treatment cabin having closed walls, a closed roof and a door for entering the treatment cabin; a cold treatment gas preparation and distribution system for preparing a cold gas mixture and introducing it into the treatment cabin; and a control system for controlling the introduction of cold treatment gas from the cold treatment gas preparation and distribution system into the treatment cabin, in which the treatment cabin further includes a breathing window for allowing a patient located inside the treatment cabin to breath air from outside of the treatment cabin, the breathing window including sealing means for allowing a tight contact between the breathing window and the face of the patient.

15 Claims, 3 Drawing Sheets

(56) References Cited

U.S. PATENT DOCUMENTS

| | | | |
|---|---|---|---|
| 2002/0193852 A1* | 12/2002 | Renfro | A61F 7/0053 607/104 |
| 2010/0313579 A1* | 12/2010 | Decourcelle | B60P 3/14 62/51.1 |
| 2011/0238143 A1* | 9/2011 | Schock | A61F 7/0053 607/104 |
| 2013/0025302 A1* | 1/2013 | Lyubchenko | A61F 7/0053 62/89 |
| 2015/0265460 A1* | 9/2015 | Erganokov | A61F 7/0053 607/87 |

* cited by examiner

CRYOGENIC DEVICE

CROSS REFERENCE TO RELATED APPLICATIONS

This is a national stage application based on PCT/EP2013/061068, filed on May 29, 2013, which claims priority to Switzerland Patent Application No. CH 02772/12, filed on Dec. 11, 2012. This application claims the priority of these prior applications and incorporates their disclosures by reference in their entireties.

The present invention relates to a cryogenic device for carrying out cryotherapy on the entire body of a patient, also known as general cryotherapy. The present invention relates in particular to a cryogenic device comprising a treatment cabin for taking up a patient, that can be used, for example, for general cryotherapy in hospitals, ambulatory medical centers, sanatoriums, spa resorts, etc.

Cryotherapy, or cryogenic therapy, is a therapeutic treatment in which a patient is subjected for a very short period of time to very low temperatures, typically between −120° C. and −140° C., sometimes down to −160° C. This induces a very fast cooling of the patient's body, whose skin temperature may go down to 0° to +2° C.

The general cryotherapy sessions are performed in dedicated cryotherapeutic devices sometimes referred to as cryogenic saunas or cryosaunas that can take up one or more patients at a time. The cryotherapeutic effect is obtained by cooling down the patient's body with a cold treatment gas, usually a mixture of air and cold nitrogen vapours, having a temperature of between −120° C. and −140° C., sometimes as low as −160° C. The procedure lasts an average of 2 to 3 minutes during which the human organism is subjected to a powerful general cryotherapeutic action, the effect of which is felt during a long period of time. The efficiency of general cryotherapy is proportional to the contact surface of the skin with the cooling environment.

General cryotherapy may be used, for example, for the treatment of illnesses such as proliferative osteoarthritis, bronchial allergy, scaly scab, hormonal disorders, or for wellness purposes. Applying general cryotherapy stimulates the immune system, the endocrine, the metabolism, and provokes endorphin saturation of blood.

Cryosaunas for individual use are usually in the form of treatment cabins in the shape of a tube with or without thermal insulation in which a patient may stand, a system for preparing, introducing and/or distributing the cold treatment gas into the cabin, and/or for evacuating gas from the cabin, and a control system for automatically controlling the parameters of the procedure.

U.S. Pat. No. 4,838,270, for example, describes a device for carrying out cryotherapy on the entire body that includes an open treatment chamber designed as a half shell comprising openings in the back for the exhaust of the treatment gas and openings in the sides for the supply of the treatment gas. A drawback of this cryogenic device is that, the treatment chamber being open, it is impossible to achieve a uniform temperature inside it, and therefore to achieve a uniform general cryogenic treatment of the patient. Furthermore, an important quantity of cold gas is rapidly lost because of the open character of the chamber, thus resulting in an important waste of energy.

The company "KRION" of Saint-Petersburg, Russian Federation, (www.krion-russia.com) produces a cryosauna named "KAEKT KRION-01". This cryogenic device comprises a tubular cabin for taking up a patient, an elevating floor for adjusting the height of the cabin to the height of the patient, a pump for pumping liquid nitrogen, a Dewar vessel for storing liquid nitrogen and a control system. In the cabin, the patient is immersed up to the shoulders in the cryogenic treatment gas. The space above the upper section of the cabin is ventilated to prevent the ingress of cryogenic gas in the patient's upper airway. A drawback of this cryogenic device is that, even though it is closed and thermally insulated on its periphery, the treatment cabin is open in its upper section, so that the cryogenic gas entering the bottom of the cabin blends with the tempered ambient air of the treatment room in the upper section. The treatment gas thereby warms up in the upper section of the treatment cabin, so that the temperature cannot be maintained uniformly within the cabin and significant temperature differences may exist between the lower and the upper sections. This causes non-uniform cryotherapeutic effect on the upper and lower parts of the patient's body. Furthermore, a patient standing in the cabin up to the shoulders, despite the ventilation above the cabin, partly breathes the cold gas mixture of nitrogen and air that is pushed by a ventilator from the lower section of the cabin to its upper section, thereby creating a risk of cold cryogenic gas entering the airway and the lungs of the patient, which may result in cryogenic lesions of the corresponding tissues.

Patent application DE 36 41 293 describes a device for general cryotherapy comprising a closed treatment cabin, which is divided in a treatment chamber in its lower section and a breathing chamber in the upper section. The sections are separated from each other by a floor with an opening for receiving the neck of a patient. Openings are provided in the cabin's roof with ventilators to draw ambient air from the treatment room into the breathing chamber. The pressure in the treatment chamber is maintained lower than the pressure in the breathing chamber in an attempt to avoid cold treatment gas from penetrating the breathing chamber. A drawback of this cryogenic device is that there is no tight separation between the treatment and the breathing chambers, so that the patient's safety is not guaranteed if, for example, the pressure difference between the two chambers cannot be maintained and/or the ventilators pulsing ambient air into the breathing chamber stop working. Furthermore, the temperature difference between the upper part and the lower part of the treatment chamber is also important because of the continuous flow, in normal operating conditions, of ambient air from the breathing chamber into the treatment chamber.

An aim of the present invention is thus to overcome the drawbacks of the prior art cryogenic devices.

An aim of the present invention is in particular to minimize the temperature difference of the cryogenic treatment gas inside the treatment cabin, in particular between the upper and lower sections.

Still another aim of the present invention is to provide comfortable breathing conditions to a patient during the cryogenic treatment and to prevent any ingress of cold treatment gas in the airway and lungs of the patient.

These aims and other advantages are achieved by a cryogenic device according to the independent claim.

These aims and other advantages are achieved in particular by a cryogenic device for carrying out cryotherapy on the entire body of a patient, the cryogenic device comprising: a treatment cabin for taking up a patient, the treatment cabin having closed walls, a closed roof and a door for entering the treatment cabin; a cold treatment gas preparation and distribution system for preparing a cold gas mixture and introducing it into the treatment cabin; and a control system for controlling the introduction of cold treatment gas from the cold treatment gas preparation and distribution system into the treatment cabin, wherein the treatment cabin further comprises a breathing window for allowing a patient located inside the treatment cabin to breath air from outside of the treatment cabin, the breathing window comprising sealing means for allowing a tight contact between the breathing window and the face of the patient.

The sealing means, for example comprises a flexible material, for example natural leather or any appropriate material, provided on the periphery of the breathing window.

In embodiments, the breathing window is an oval opening formed through the walls of the treatment cabin. In embodiments, the size and/or shape of the breathing window is adjustable to the size and/or shape of the face of a patient.

The treatment cabin preferably comprises a depressurization valve, for example a gravitational valve, in the roof.

The treatment cabin preferably comprises thermal insulation for thermally insulating its enclosure from its environment.

In embodiments, the treatment cabin further comprises an elevating floor for adjusting the distance between the elevating floor and the breathing window to the height of the patient.

The control system is, for example configured for automatically controlling a cryotherapeutic procedure according to a predetermined program.

In embodiments, the door further comprises a safety handle inside the treatment cabin for allowing an emergency opening of the door from inside the treatment cabin.

Thanks to the closed treatment cabin with sealing means on the breathing window, the gaseous exchanges between the enclosure of the cabin and its environment are almost inexistent, thereby allowing a homogenous distribution of the cold treatment gas inside the treatment cabin. The temperature difference between the lower part and the upper part of the treatment cabin during the cryotherapeutic treatment can thus be lower than 10° C., which is significantly less than what can be achieved with prior art cryogenic devices. The cryotherapeutic effect achieved with the cryogenic device of the invention is, thus, uniform on the entire body of the patient and the temperature difference is not felt in practice. The cryogenic device of the invention is, thus, more efficient than prior art devices in obtaining the sought cryotherapeutic effect.

The cryogenic device of the invention is furthermore safe and comfortable for the patient, because the patient whose body is completely wrapped by the cold treatment gas, breathes ambient air, for example the air of the treatment room in which the treatment chamber is installed, through the breathing window, while the sealing means around the breathing window prevents cold treatment gas from exiting the treatment cabin 1 through the breathing window, and thus completely eliminates any risk of contact between the upper airway of the patient and the cold cryogenic treatment gas.

The present invention will be better understood with the help of the following description of preferred embodiments, illustrated by the figures where:

Figure 1:
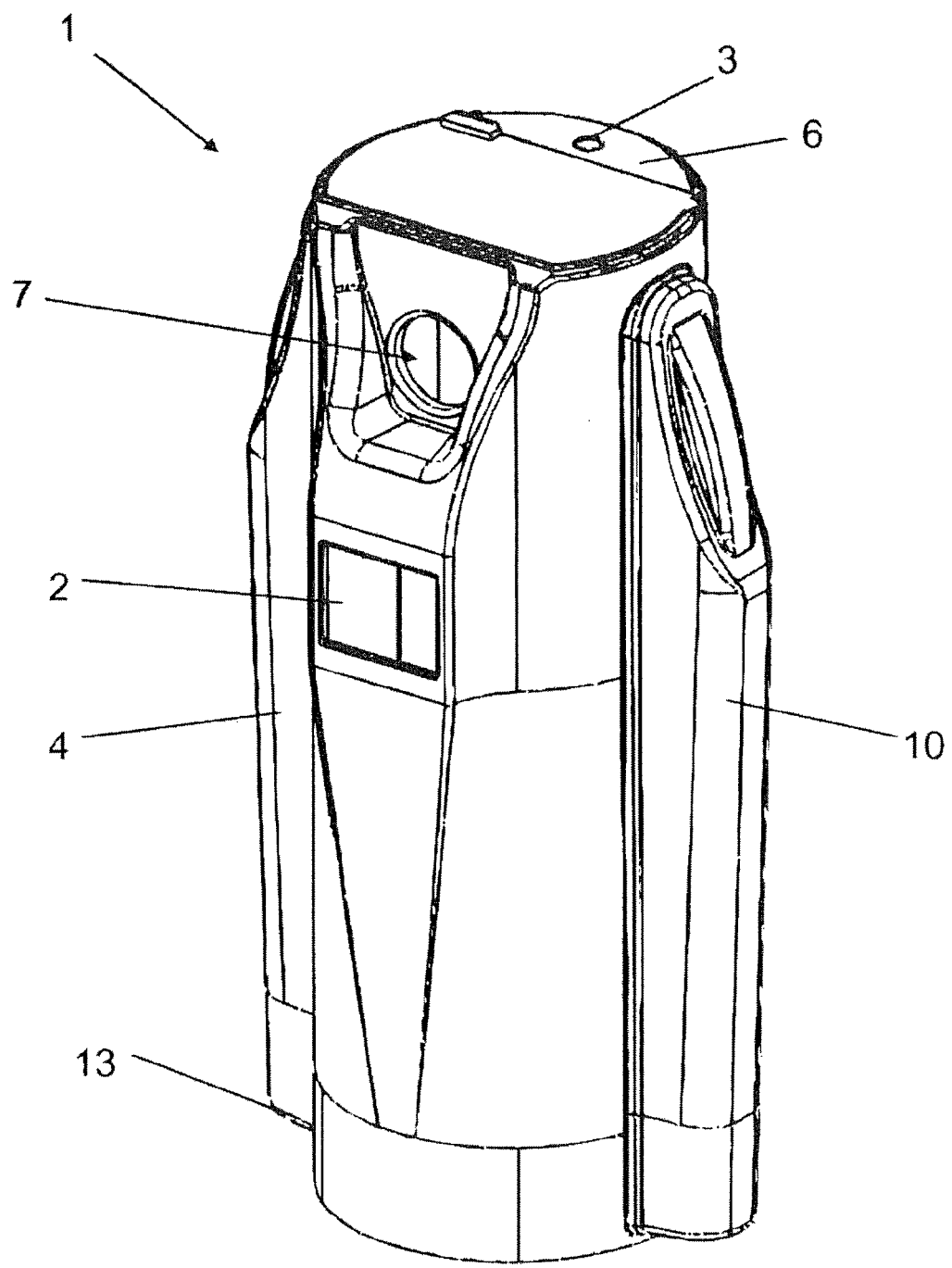
FIG. 1 is a perspective view of a cryogenic device according to an embodiment of the invention.
Figure 2:
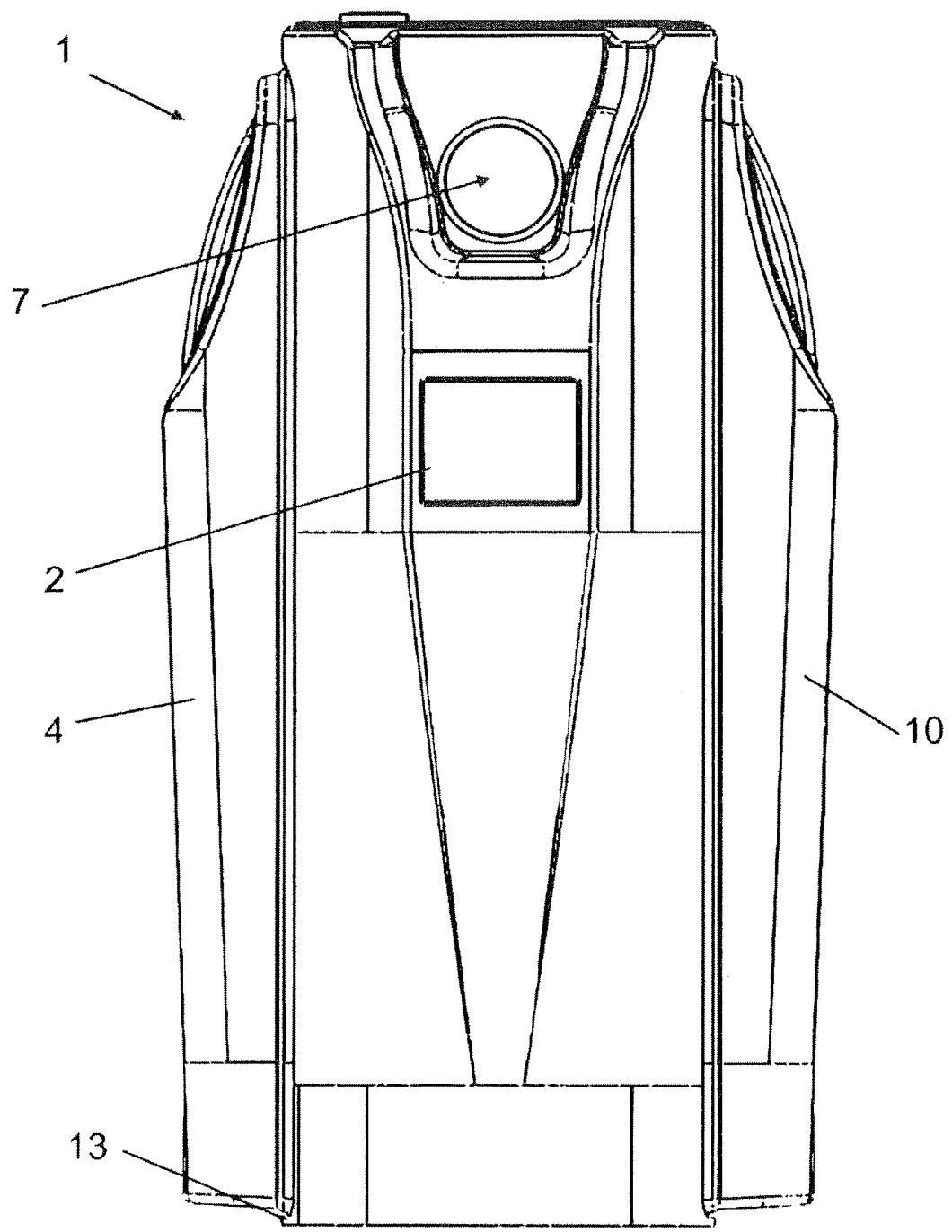
FIG. 2 is a front view of the cryogenic device of FIG. 1.
Figure 3:
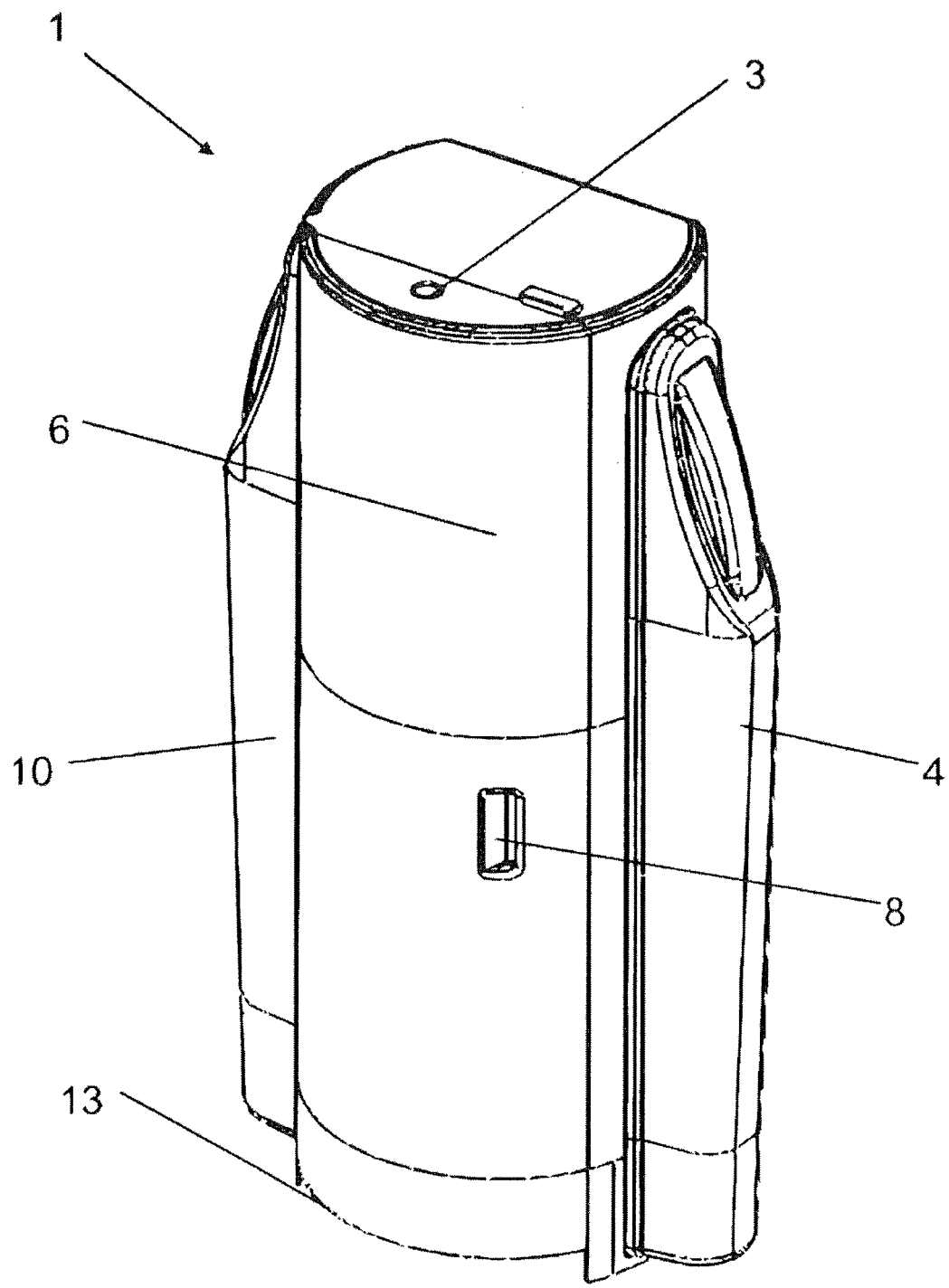
FIG. 3 is a perspective view from behind of the cryogenic device of FIG. 1.

FIGS. 1, 2 and 3 illustrate a cryogenic device according to an embodiment of the invention. According to the invention, the cryogenic device comprises a treatment cabin 1 with closed walls and roof, forming an enclosure for taking up a patient. According to the illustrated embodiment, the treatment cabin 1 is for example built on a chassis 13 standing on adjustable feet that are not visible on the picture. The treatment cabin 1 is thus self-standing and can be placed in any appropriate location without requiring any additional fixtures, and it can be displaced if necessary without having to be dismounted. Other constructions are however possible within the frame of the invention. In embodiments, the treatment cabin is for example a fixed appliance built directly on site, which may, for example be at least partly united with the walls of the treatment room.

The treatment cabin 1 comprises a door 6 with a handle 8 on its external side for opening and closing the door 6 from outside the treatment cabin 1. In the illustrated embodiment, the door 6 is located on the back side of the treatment cabin 1 and takes up the entire height of the cabin. Other door configurations and/or locations are however possible within the frame of the invention for allowing a patient to enter the treatment cabin. The door can for example be located in the front side and/or in one of the lateral sides of the treatment cabin 1. In embodiments, the door 6 further comprises an emergency handle on its internal side, which is not visible in the figures, for allowing a patient to open the door 6 from inside the treatment cabin 1 and to thereby, for example, interrupt the cryotherapeutic procedure in case of emergency.

According to the invention, the treatment cabin 1 comprises a breathing window 7 for al lowing a patient located in the treatment cabin 1 to breathe the ambient air from outside the treatment cabin 1, for example the air of the treatment room in which the treatment cabin 1 is standing. The breathing window is for example located in the front side of the treatment cabin 1. The breathing window 7 thus forms an opening through the wall of the treatment cabin 1, The breathing window 7 is configured to allow a patient standing in the treatment cabin 1 to place his or her face in the opening. The breathing window 7 is for example a round or oval opening, By placing his or her face in the breathing window 7, the patient can preferably look outside the treatment cabin 1 and/or talk with an operator supervising the cryogenic treatment procedure, while the treatment cabin is closed. This provides for an accrued comfort to the 5 patient. Furthermore, the breathing window 7 allows an operator supervising the cryogenic treatment procedure to see the patient's face and thereby quickly detect and react to any problem that may occur by controlling the patient's facial expressions and/or talking to him or her during the cryogenic treatment, thereby improving the overall safety of the device.

The breathing window 7 preferably comprises sealing means for achieving a tight contact between the edge of the breathing window 7 and the face of a patient standing inside the treatment cabin 1. The sealing means thus participates to the thermal insulation of the treatment cabin by preventing cold treatment gas from exiting the treatment cabin 1 through the breathing window 7 during a cryogenic treatment procedure if the patient standing in the treatment cabin 1 correctly placed his or her face in the breathing window 7. The sealing means further provides safety to the patient treated in the treatment cabin 1 by preventing the patient from inhaling a cold treatment gas while breathing the ambient air through the breathing window 7. In embodiments, the sealing means comprises a flexible sealing material on the periphery of the breathing window 7, for example natural leather. The sealing material preferably remains flexible when subjected to very low temperatures and/or has a very low thermal conductivity for providing the highest possible comfort to the patient and provide optimal sealing of the treatment cabin 1.

In embodiments, the shape and/or size of the breathing window 7 may be adjusted to the size and/or shape of the patient's face in order to optimize comfort to the patient while still achieving a tight contact between the breathing window 7 and the patient's face. The breathing window's 7 shape and/or size may for example be adjusted by placing sealing means of different shape and/or sizes on its periphery, or by any other appropriate means.

In embodiments, the treatment cabin 1 comprises an elevating floor, or moving floor, inside the treatment cabin 1, which is not visible in the figures, in order to adjust the distance between the elevating floor and the breathing window 7 to the height of the patient, thereby allowing the patient to correctly place his or her face in the breathing window 7 when standing in the treatment cabin 1. The height of the elevating floor is for example adjustable by actuating one or more corresponding commands located for example on the outside of the treatment cabin 1, for example next to the handle 8 of the door 6, or inside the treatment cabin 1.

In embodiments, a gravitational depressurizing valve 3 is placed in the roof of the treatment cabin 1 for avoiding pressures higher than a predetermined threshold within the treatment cabin 1, in particular during introduction of the cold treatment gas. The depressurizing valve 3 is preferably located at the highest part of the roof in order to first evacuate the warmer air that tends to accumulate at the top of the treatment cabin 1. The depressurizing valve 3 is for example gravitational, for example with a threshold pressure value of 0.7 atm.

In embodiments, the cryogenic device of the invention comprises a cold treatment gas preparation and distribution system for preparing the cryogenic treatment gas and distributing it inside the treatment cabin 1. The cold treatment gas preparation and distribution system for example comprises a Dewar container or any appropriate container for storing liquid nitrogen, which is not represented on the figures, a heat exchanger 10 for mixing nitrogen vapors with air up to a desired temperature, wherein the heat exchanger 10 is connected to the nitrogen container through a duct, not visible on the figures, for example a flexible hose, for bringing nitrogen from the container to the heat exchanger 10, and a pipe network connected to the heat exchanger 10 for distributing, preferably uniformly distributing, the cold treatment gas inside the treatment cabin 1.

The nitrogen container is for example a standalone container standing next to the treatment cabin 1, which is directly connected to the heat exchanger 10 over a single duct that is releasably attached to the treatment cabin 1 by an appropriate connector. In other embodiments, the nitrogen container is a remote container that provides nitrogen to one or more cryogenic devices and/or other appliances. The heat exchanger 10 is located within the walls of the treatment cabin 1, for example on the right hand side of the treatment cabin 1. An advantage of this configuration is its compactness and self-contained nature, wherein all components of the cryogenic device, except for the nitrogen container, are contained within the walls of the treatment cabin 1.

Other configurations are however possible within the frame of the invention. In embodiments, the heat exchanger 10 is for example located outside the treatment cabin 1, inside or outside the treatment room, and the prepared cold treatment is fed to the treatment cabin 1 over appropriated ducts and one or more openings through the walls of the treatment cabin 1.

In embodiments, the cryogenic gas prepared in the heat exchanger 10 circulates in a piping system within the treatment cabin 1 and is distributed inside the enclosure of the treatment cabin 1, for example through vertical tubes that are regularly spread around the periphery of the enclosure and each comprise a plurality of openings, or nozzles, distributed along their length, thereby providing for a uniform distribution of the treatment gas within the enclosure. The piping system and/or the vertical tubes are preferably located within the walls of the treatment cabin 1 in order to avoid as much as possible any contact between the pipes and the patient. Any other distribution system is however possible within the frame of the invention for achieving a uniform distribution of the treatment gas inside the enclosure formed within the closed treatment cabin 1.

The cryogenic device of the invention further comprises a control system 4 for controlling the operation of the cryogenic device. In the illustrated embodiment, the control system 4 is for example located within the walls on the left hand side of the treatment cabin 1. Other locations inside or outside the treatment cabin are however possible within the frame of the invention. In other embodiments, the control system is for example located outside the treatment cabin, for example as a standalone operating unit placed next to the treatment cabin and comprising, for example a desk with a display device and one or more user interfaces. The control system 4 is for example a computer-based system with a user interface and interfaces to various elements of the cryogenic device for controlling their operation and/or sensors for monitoring specific parameters. The control system 4 for example controls and/or monitors the temperature in one or more locations inside the treatment cabin 1, the time of the cryotherapeutic procedure, the locking/unlocking of the door 6, etc.

In embodiments, the control system 4 comprises software modules that, when run on a processor of the control system 4, allow the automatic operation of the cryogenic device, for example the automatic control and monitoring of a predetermined cryotherapeutic procedure.

In embodiments, the control system 4 comprises a display device 2 for displaying information to a user, for example to an operator supervising the cryogenic treatment, and/or to a patient located in the treatment cabin 1. The display device 2 for example comprises a touch screen located on the treatment cabin 1, for example on its front side. The touch screen preferably also allows entering commands before and/or during a cryogenic treatment procedure and is thus used as a user interface of the control system 4. Other user interfaces are however possible within the frame of the invention, such as, for example but not exclusively, touch keys and/or a keyboard located on the treatment cabin 1, for example in the vicinity of the display device 2, a remote control, an application running on a remote device, or any combination thereof.

Optionally, the control system of the invention comprises a timer, for example with a countdown and an acoustic signal, for measuring the treatment time and signaling once it is elapsed, and a clock.

In embodiments, the cryogenic device of the invention functions as follows.

A patient enters the treatment cabin 1 through the door 6.

The operator adjusts, for example with the corresponding commands, the height of the internal space, or enclosure, of the treatment cabin 1 to the height of the patient by adjusting the height of the elevating floor, in order to position the patient's face at the level of the breathing window 7, which ensures sealing of the treatment cabin 1 and security of the patient during the cryogenic treatment procedure.

The patient places his or her face in the breathing window 7, which allows him or her to breathe the ambient air from outside the treatment cabin 1, for example the air of the treatment room in which the treatment cabin 1 is standing, thereby preventing cold treatment gas from penetrating the patient's airway and excessively cooling them.

The door 6 of the treatment cabin 1 is closed, for example with the external handle 8, preferably by an operator leading the procedure.

Liquid nitrogen is taken out of the container preferably with a specific siphon comprising a heat resistor that heats the liquid nitrogen. The pressure of the heated nitrogen consequently increases in the siphon, which in turn pushes the liquid nitrogen through the tubing and then into the heat exchanger 10. The control system 10 preferably automatically controls the taking of nitrogen and maintains a predetermined pressure in the nitrogen container. Optionally, the cryogenic device of the invention comprises a surge protector for preventing the heat resistor from overheating.

In the heat exchanger 10, the liquid nitrogen evaporates and is mixed with the ambient air. The thus obtained cryogenic gas, or cold treatment gas, is circulated inside the treatment cabin 1 through the pipe system and distributed by, for example, vertically aligned nozzles that are located for example in the upper and middle parts of the treatment cabin 1. The cold treatment gas is distributed, for example in swirls, along the inside walls of the treatment cabin 1 and comes in contact with the patient's skin, thereby creating the cryotherapeutic effect.

The temperature inside the treatment cabin 1 is preferably automatically controlled by the control system 10, according, for example, to the prescriptions of a chosen cryotherapeutic program, and can preferably also be controlled visually by the operator, for example with the help of the display device 2 that displays for example the temperature measured by one or more thermometers located inside the treatment cabin 1 and/or in the heat exchanger 10.

The excess pressure generated by the introduction of the cold treatment gas inside the treatment cabin 1 is evacuated by the depressurizing valve 3.

Once a preset time for the cryogenic treatment is elapsed, for example two or more minutes, the distribution of cold treatment gas is stopped and the door 6 is opened for allowing the patient to come out of the treatment cabin 1.

The cryogenic device of the invention is preferably automatically controlled by the control system during the cryotherapeutic treatment, but the operator may for example override the automatic control and set it to manual mode, for example in case of emergency.

In embodiments, the patient may come out of the treatment cabin 1 by himself in case of emergency, with the help of the safety handle located on the door 6, inside the treatment cabin 1. The duration of the cryotherapeutic session is determined by the control system according to predetermined programs, or manually entered by an operator.

The invention claimed is:

1. Cryogenic device for carrying out cryotherapy on the entire body of a patient, said cryogenic device comprising:
   a treatment cabin for taking up a patient, said treatment cabin having closed walls, a floor, a closed roof and a door for entering the treatment cabin;
   a depressurization valve in said roof;
   a cold treatment gas preparation and distribution system for preparing a cold gas mixture and introducing said cold gas mixture into said treatment cabin; and
   a control system for controlling the introduction of cold treatment gas from said cold treatment gas preparation and distribution system into the treatment cabin;
   wherein said treatment cabin further comprises a breathing window formed in said wall for allowing a patient located inside said treatment cabin to breathe air from outside of said treatment cabin, said breathing window comprising a sealing material on the periphery of said breathing window for allowing a tight contact between said breathing window and the face of said patient.

2. Cryogenic device according to claim 1, wherein said sealing material is a flexible material provided on the periphery of said breathing window.

3. Cryogenic device according to claim 2, wherein said flexible material is natural leather.

4. Cryogenic device according to claim 3, wherein said breathing window is an oval opening formed in said wall of said treatment cabin.

5. Cryogenic device according to claim 3, wherein the size and/or the shape of said breathing window is adjustable to the size and/or shape of the face of a patient.

6. Cryogenic device according to claim 2, wherein said breathing window is an oval opening formed in said wall of said treatment cabin.

7. Cryogenic device according to claim 2, wherein the size and/or the shape of said breathing window is adjustable to the size and/or shape of the face of a patient.

8. Cryogenic device according to claim 1, wherein said breathing window is an oval opening formed in said wall of said treatment cabin.

9. Cryogenic device according to claim 8, wherein the size and/or the shape of said breathing window is adjustable to the size and/or shape of the face of a patient.

10. Cryogenic device according to claim 1, wherein the size and/or the shape of said breathing window is adjustable to the size and/or shape of the face of a patient.

11. Cryogenic device according to claim 1, wherein said depressurization valve is a gravitational valve.

12. Cryogenic device according to claim 1, said treatment cabin further comprising thermal insulation for thermally insulating the enclosure of said treatment cabin from its environment.

13. Cryogenic device according to claim 1, wherein said floor is an elevating floor for adjusting the distance between said elevating floor and said breathing window to the height of the patient.

14. Cryogenic device according to claim 1, said control system being configured for automatically controlling a cryotherapeutic procedure according to a predetermined program.

15. Cryogenic device according to claim 1, said door further comprising a safety handle inside said treatment cabin for allowing emergency opening of said door from inside said treatment cabin.

* * * * *